(12) United States Patent
Kwiatkowski

(10) Patent No.: US 7,824,626 B2
(45) Date of Patent: Nov. 2, 2010

(54) AIR HANDLER AND PURIFIER

(75) Inventor: Krzysztof C. Kwiatkowski, Austin, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 0 days.

(21) Appl. No.: 12/210,762

(22) Filed: Sep. 15, 2008

(65) Prior Publication Data
US 2009/0123343 A1    May 14, 2009

Related U.S. Application Data

(60) Provisional application No. 60/975,697, filed on Sep. 27, 2007.

(51) Int. Cl.
*A61L 9/16* (2006.01)
(52) U.S. Cl. .............. 422/120; 422/122; 422/292; 96/224; 95/273; 95/285
(58) Field of Classification Search ............ 422/120, 422/122, 292; 96/224; 95/273, 285
See application file for complete search history.

(56) References Cited

U.S. PATENT DOCUMENTS

| | | | |
|---|---|---|---|
| 3,261,978 A | 7/1966 | Brenman | |
| 3,416,503 A | 12/1968 | High | |
| 4,954,465 A * | 9/1990 | Kawashima et al. | 502/5 |
| 5,600,200 A | 2/1997 | Kumar et al. | |
| 5,650,126 A | 7/1997 | Taoda et al. | |
| 5,656,242 A | 8/1997 | Morrow et al. | |
| 5,658,530 A | 8/1997 | Dunn | |
| 5,688,308 A | 11/1997 | Voigts | |
| 5,866,984 A | 2/1999 | Doughty et al. | |
| 5,919,422 A | 7/1999 | Yamanaka et al. | |
| 6,022,511 A | 2/2000 | Matschke | |
| 6,094,767 A | 8/2000 | Iimura | |
| 6,103,391 A | 8/2000 | Hirayama | |
| 6,171,684 B1 | 1/2001 | Kahlbaugh et al. | |
| 6,228,480 B1 * | 5/2001 | Kimura et al. | 428/328 |
| 6,242,862 B1 | 6/2001 | Kawakatsu | |
| 6,294,246 B1 | 9/2001 | Watanabe et al. | |

(Continued)

FOREIGN PATENT DOCUMENTS

| | | | |
|---|---|---|---|
| JP | 2004181301 A | * | 7/2004 |
| WO | WO 02/102510 | | 12/2002 |
| WO | WO 2004/026471 | | 4/2004 |
| WO | WO 2006/060103 | | 6/2006 |
| WO | WO 2007/026387 A2 | * | 3/2007 |

OTHER PUBLICATIONS

Kudo et al., "Development of rectangular column structured titanium oxide photocatalysts anchored on silica sheets by a wet process," Res. Chem. Intermed. vol. 29, No. 6, pp. 631-639 (2003).

(Continued)

*Primary Examiner*—Sean E Conley
(74) *Attorney, Agent, or Firm*—Kelly Kordzik; Matheson Keys Garsson & Kordzik PLLC

(57) ABSTRACT

A system that captures and eliminates indoor pollutants and chemical and biological agents within a HVAC system by breaking down the pollutants and chemical and biological threats into non-hazardous molecules. The surface area created by crystalline titanium dioxide nano-structures results in highly effective elimination rates when catalytic ionization by UV exposure occurs. The catalyst is activated with UVA light.

17 Claims, 7 Drawing Sheets

U.S. PATENT DOCUMENTS

| | | | |
|---|---|---|---|
| 6,343,400 | B1 | 2/2002 | Massholder et al. |
| 6,355,308 | B1 | 3/2002 | Sato et al. |
| 6,468,428 | B1 | 10/2002 | Nishii et al. |
| 6,488,900 | B1 | 12/2002 | Call et al. |
| 6,521,321 | B2 | 2/2003 | Kahlbaugh et al. |
| 6,528,021 | B1 | 3/2003 | Williams |
| 6,558,639 | B1 * | 5/2003 | Watanabe et al. ........ 422/186.3 |
| 6,589,489 | B2 | 7/2003 | Morrow et al. |
| 6,589,906 | B2 | 7/2003 | Sato et al. |
| 6,607,702 | B1 | 8/2003 | Kang et al. |
| 6,675,425 | B1 | 1/2004 | Iimura |
| 6,761,859 | B1 | 7/2004 | Oda |
| 6,766,097 | B2 | 7/2004 | Horton, III |
| 6,783,363 | B2 | 8/2004 | Eguchi et al. |
| 6,821,320 | B1 | 11/2004 | Miyazaki |
| 6,843,981 | B1 | 1/2005 | Ishibashi et al. |
| 6,846,500 | B1 | 1/2005 | Luo et al. |
| 6,866,828 | B2 | 3/2005 | Segawa |
| 6,902,397 | B2 | 6/2005 | Farrell et al. |
| 6,908,881 | B1 | 6/2005 | Sugihara |
| 6,939,397 | B2 * | 9/2005 | Nelsen et al. ................. 96/224 |
| 6,951,463 | B2 | 10/2005 | Masuhara et al. |
| 7,300,634 | B2 | 11/2007 | Yaniv et al. |
| 7,354,448 | B2 | 4/2008 | Altshuler et al. |
| 2002/0037244 | A1 | 3/2002 | Takahashi et al. |
| 2002/0070648 | A1 | 6/2002 | Forsberg |
| 2002/0081246 | A1 | 6/2002 | Tsukada et al. |
| 2002/0094298 | A1 | 7/2002 | Monagan |
| 2003/0146082 | A1 | 8/2003 | Gibson et al. |
| 2003/0203205 | A1 | 10/2003 | Bi et al. |
| 2004/0007453 | A1 | 1/2004 | Scahill et al. |
| 2004/0110458 | A1 | 6/2004 | Kato et al. |
| 2004/0118285 | A1 | 6/2004 | Kim et al. |
| 2004/0131811 | A1 | 7/2004 | Lee et al. |
| 2004/0170537 | A1 | 9/2004 | Hara |
| 2004/0171505 | A1 | 9/2004 | Nonami et al. |
| 2004/0175288 | A1 | 9/2004 | Horton, III |
| 2004/0211728 | A1 | 10/2004 | Liu et al. |
| 2004/0241040 | A1 | 12/2004 | Wei et al. |
| 2009/0136389 | A1 * | 5/2009 | Park ........................... 422/122 |

OTHER PUBLICATIONS

Blake et al., "Application of the photocatalytic chemistry of titanium dioxide to disinfection and the killing of cancer cells," 1999, vol. 28, No. 1, pp. 1-50.

Bonard et al., "Field Emission From Cylindrical Carbon Nanotube Cathodes: Possibilities for Luminescent Tubes," Applied Physics Letters, vol. 78, No. 18, Apr. 30, 2001, pp. 2775-2777.

Croci et al., "A Fully Sealed Luminescent Tube Based on Carbon Nanotube Field Emission," Microelectronics Journal, vol. 35, Issue 4, Apr. 2004, pp. 329-336.

Jo, et al., "Field Emission of Carbon Nanotubes Grown on Carbon Cloth," Applied Physics Letters, 85 (2004), pp. 810-812.

Jo, et al., "Field Emission of Zinc Oxide Nanowires Grown on Carbon Cloth," Applied Physics Letters, 85 (2004), pp. 1407-1409.

* cited by examiner

Fig. 6

AIR HANDLER AND PURIFIER

This application claims priority to U.S. provisional application Ser. No. 60/975,697.

BACKGROUND

EPA data show that people are subjected to a variety of health risks when driving in cars, flying in planes or being exposed to a variety of indoor pollutants when in home or at work environments. In addition, infectious diseases caused by various bacteria, viruses and spores in the hands of terrorists have become serious threats. The purposeful release of threat agents is an important problem of national, strategic importance. Conventional technology for protection is based on high efficiency filtration. However, filtration just captures the biological threats, it does not neutralize them. The bacteria and viruses captured in those filters may come off the filter and back into the air.

BRIEF DESCRIPTION OF THE DRAWINGS

FIG. 6 illustrates a reduction of anthrax spores when immobilized on catalyst and exposed to UV light at 365 nm. % reduction.

DETAILED DESCRIPTION

It is essential to maintain good indoor air quality and to protect homeland and overseas U.S. targets from chemical and biological attacks. Embodiments of the present invention greatly increase both the indoor air quality and the protection of high profile stationary targets. This technology will mitigate attacks via HVAC systems. Within an HVAC system, the conventional approach for air quality improvement or defending against chemical or biological attacks is to capture gases and particulates. HVAC systems using HEPA filters and activated charcoal attempt to capture threats for subsequent disposal. In addition, the air can be treated with germicidal UV lamps which will decrease survival rate of biological organisms but, at the same time, increase indoor ozone levels and therefore health risks. Embodiments of the present invention will capture and eliminate indoor pollutants and chemical and biological agents within a HVAC system. Embodiments of the present invention work, by breaking down the pollutants and chemical and biological threats into non-hazardous molecules such as carbon dioxide and water. The surface area created by crystalline titanium dioxide nanostructures results in highly effective elimination rates when catalytic ionization by UV exposure occurs. The invention's catalyst is activated with UVA light, which does not possess health risks due to ozone production of some germicidal UV lamps. However, in some applications like bio threat mitigation, a user may choose to enhance the system efficiency by incorporating germicidal lamps. Therefore, embodiments of the present invention will maintain good indoor air quality at homes, office buildings, plane interior air or automobile interior air. In addition, the embodiments of the present invention will mitigate attacks via HVAC systems on government buildings and high profile stationary targets.

Embodiment 1

Figure 1:
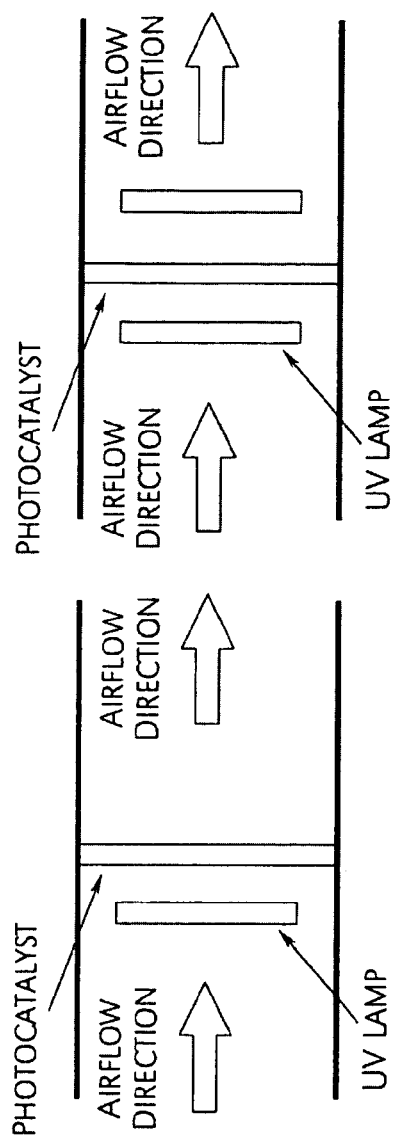
FIG. 1 illustrates a design of the antimicrobial unit showing two arrangements of UV light sources.

Flow-through photocatalyst filter for collection/inactivation/decomposition of biological contaminants and decomposition of air contaminants:

To achieve biological contaminants collection rate of 99.5%, designed is a flow-through filter depicted in FIG. 1. This approach expands the application of the invention to biological contaminants like bacteria, viruses and spores. The new design provides a high collection efficiency for biological air contaminants and increases their contact with the photocatalyst resulting in their subsequent destruction.

FIG. 1 illustrates a design of the antimicrobial unit showing two arrangements of UV light sources. This design utilizes a flow-through filter to maximize the contact time of contaminants with the photocatalyst.

Figure 2:
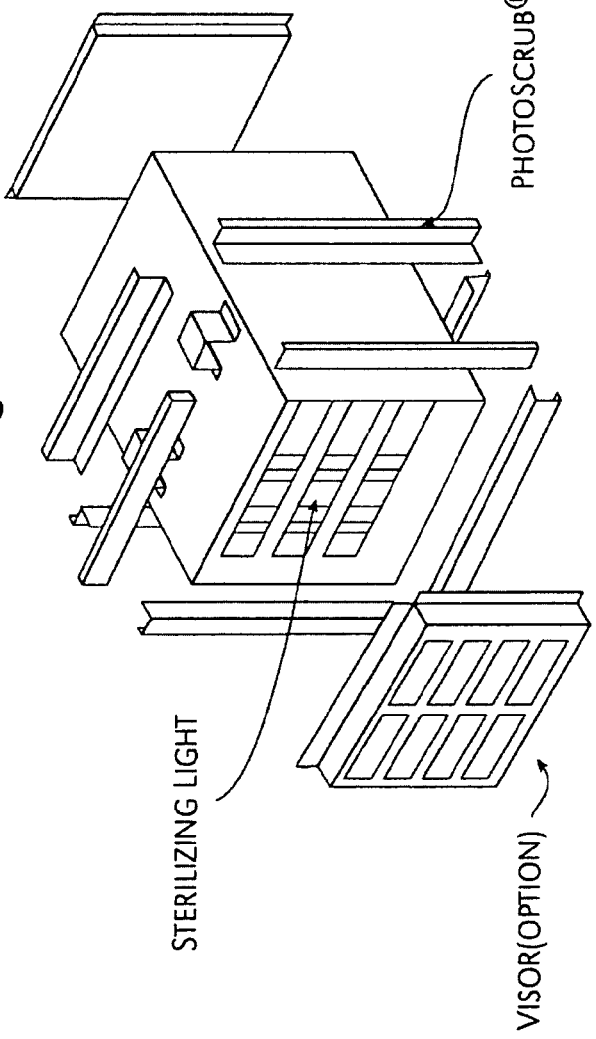
FIG. 2 illustrates an example of an assembled Biological Elimination Unit (BEU) based on the design depicted in FIG. 1.

An example of an assembled Biological Elimination Unit (BEU) based on the design depicted in FIG. 1 is shown in FIG. 2.

The material for a flow-through catalyst support may be selected from a variety of choices including, but not limiting to, commercial semi-HEPA filters, commercial HEPA filters, and commercial enzyme HEPA filters, all providing a high efficiency particulate trapping. Two factors are important in determination of the right support material for the photocatalyst: performance in collection of *Bacillus subtilis* spores used as example for a bio contaminant (Table 1) and the pressure loss across the filter (Table 2). Commercially available semi-HEPA filters may be used as flow through supports for the application of the flow through filter design. However, other materials are possible for this application if they provide a high collection rate of spores at low pressure loss across the material with deposited catalyst.

TABLE 1

*Bacillus subtilis* collection performance of the examined filters

| Filters (TiO$_2$ coating volume) | Spores concentration in upstream [cfu/ml] | Spores concentration in downstream [cfu/ml] | Trapping |
|---|---|---|---|
| Semi-HEPA w/o any coating | $3.6 \times 10^4$ | $1.2 \times 10^1$ | 99.97% |
| Semi-HEPA (coated with 18 g/m$^2$ titania) | $6.7 \times 10^4$ | $2.4 \times 10^1$ | 99.96% |
| Semi-HEPA (coated with 35 g/m$^2$ titania) | $2.4 \times 10^4$ | $2.8 \times 10^1$ | 99.88% |
| HEPA w/o any coating | $5.2 \times 10^4$ | $1.0 \times 10^0$ or less | 99.998% or more |
| HEPA (coated with 10 g/m$^2$ titania) | $4.4 \times 10^4$ | $1.0 \times 10^0$ or less | 99.998% or more |
| Enzyme HEPA | $1.8 \times 10^4$ | $1.0 \times 10^0$ or less | 99.994% or more |

TABLE 2

Pressure loss data for the examined filters

| Filters (TiO$_2$ anchored volume) | Pressure loss [Pa] |
|---|---|
| Semi-HEPA w/o coating | 48 |
| Semi-HEPA (coated with 18 g/m$^2$ titania) | 52 |
| Semi-HEPA (coated with 35 g/m$^2$ titania) | 62 |
| HEPA w/o anchoring | 144 |
| HEPA (coated with 10 g/m$^2$ titania) | 166 |
| Enzyme HEPA | 124 |

The photocatalyst was deposited on one side of the chosen support material. Four UV light tubes were providing the activation of the catalyst. Two kinds of BEU units Were assembled; the first model was using 365 nm light to activate the photocatalyst and the other 254 nm germicidal light to activate the catalyst.

Figure 3:
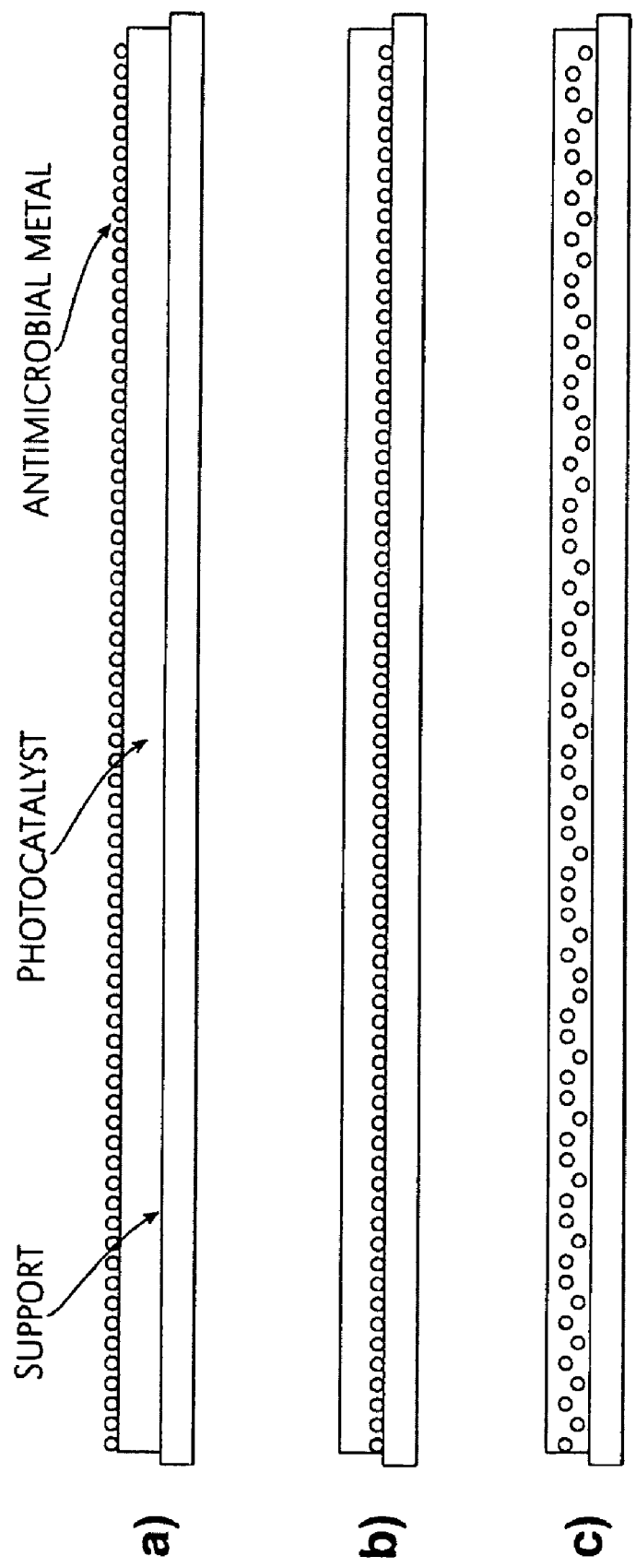
FIG. 3 illustrates three filter structure configurations.

The photocatalyst based flow through filter demonstrates very high collection efficiency for biological materials. However, to achieve a high inactivation rate of collected biological material in a reasonable short time, the filter may be modified with an antimicrobial metal. Examples of antimicrobial metals include, but are not limited to, silver, platinum, and copper. The metal may be deposited on top of the photocatalyst layer, below the photocatalyst layer, or co-deposited together with the photocatalyst as depicted in FIG. 3.

Watanabe et al. disclose in U.S. Pat. No. 6,294,246 a multifunctional material with a photocatalytic function, where a photocatalytic layer comprises photocatalytic particles and smaller particles between the photocatalytic particles, whereas the smaller particles are silver particles or they contain metal ions. In this case, both photocatalytic particles and the smaller particles are subjected to UV radiation from the UV light source, and this significantly reduces the efficiency of the filter as silver ions are reduced under the UV radiation to silver metal particles. Silver ions are generally considered as having much higher germicidal activity than metallic silver particles. In order to avoid the reduction of silver to silver metal, a strong UV radiation absorber such as titanium dioxide is placed on top of the layer containing photosensitive ionic silver.

Figure 8:
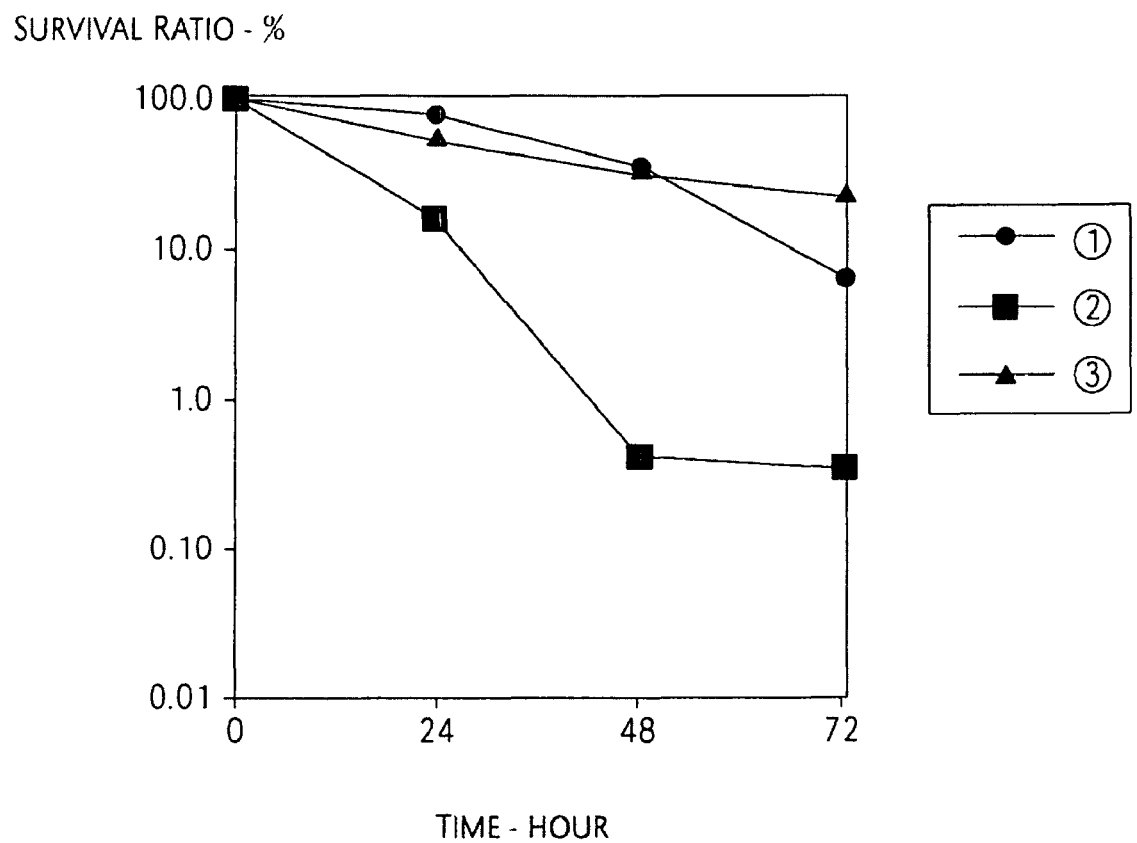
FIG. 8 shows results for testing different filter structures.

This difference in the filter efficiency has been proven in the following series of experiments. Three filter structure configurations as described in FIG. 3 have been tested. One of them, as in FIG. 3(c) has a structure similar to the one disclosed by Watanabe et al. The efficiency of this structure was found to be similar to the efficiency of the photocatalyst only without adding silver. After testing different filter structures, it was found that the structure shown in FIG. 3(b), where ionic silver layer was covered by the layer of UV absorber—photocatalyst, has highest spore inactivation efficiency. The results for these tests are shown in FIG. 8 (The experimental data shown in FIG. 8(3) correspond to structure shown in the FIG. 3(b)).

Figure 5:
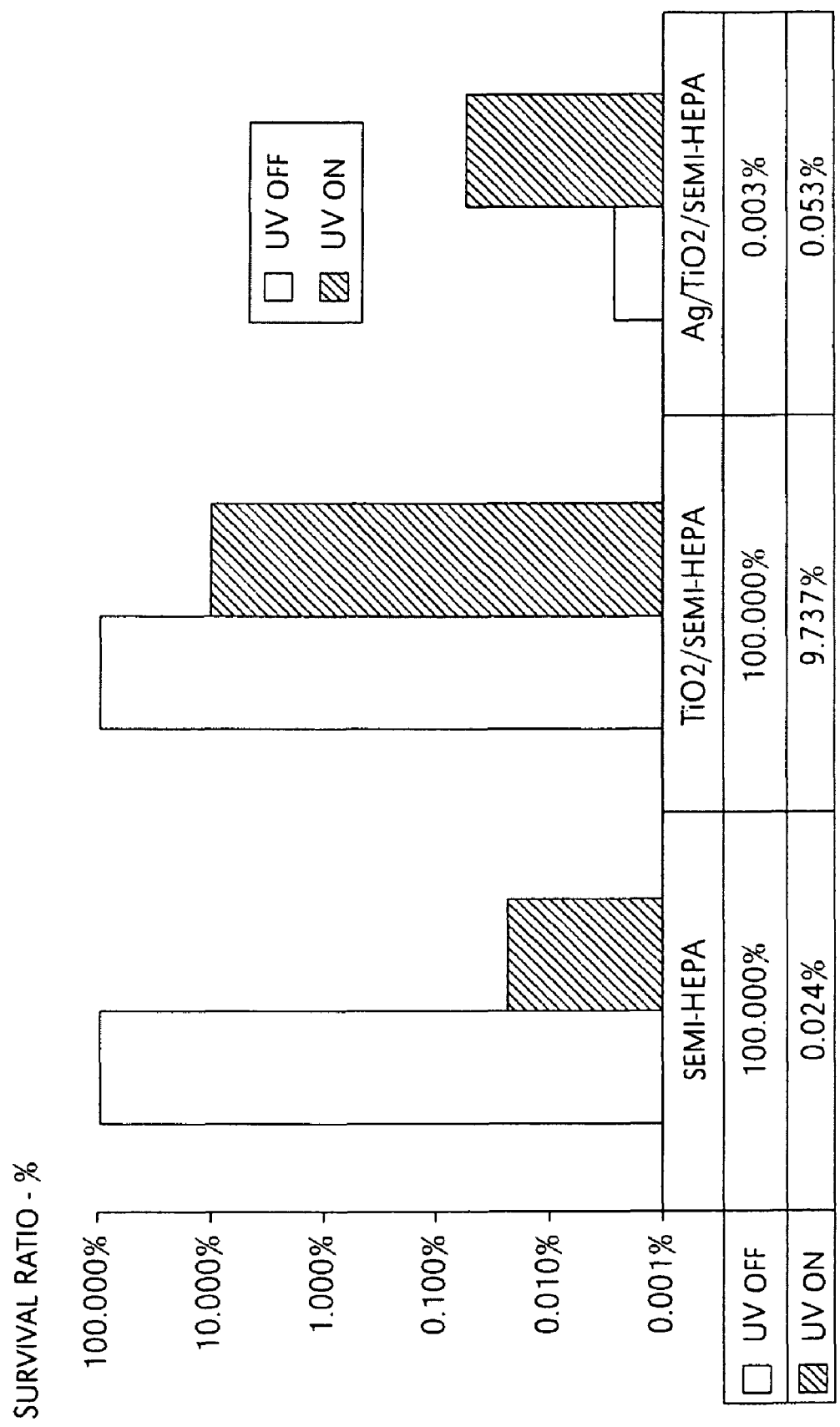
FIG. 5 illustrates *Bacillus subtilis* spores killing performance of the tested optimized filters.

An example of an effect of Ag and titania at optimized loadings on *Bacillus subtilis* deactivation/decomposition using arrangement B from FIG. 5 may be used.

Procedure: 10 ml *Bacillus subtilis* solution (10$^7$ pcs/ml) were transferred into two sets of three quartz bottles. Bare semi-HEPA was added to the first bottle. The semi-HEPA filter coated with TiO$_2$ was added to the second bottle. The semi-HEPA filter coated with TiO$_2$/Ag modified semi-HEPA filter was added to the third bottle. The first set of three bottles was agitated in dark conditions, and the second set was exposed to UV irradiation (intensity: 0.5 mW/cm$^2$, wavelength: 254 nm) during the agitation. The samples of *Bacillus subtilis* solutions were collected after 1 hour, and the remaining protein amount was determined using DC Protein Assay (manufactured by Bio-Rad Laboratories Inc.). The calorimetric procedure method flow chart is, shown in FIG. 4 and the method conditions in Table 3. The results are presented in FIG. 5.

TABLE 3

Conditions of colorimetric method

| Items | Conditions |
|---|---|
| Filter | Semi-HEPA filter FP-14S-A (Oshitari Ltd) |
| Sample size | 1.5 cm × 3 cm |
| Reaction | Quartz glass: 5 × 5 × 0.05 cm |
| Container | Glass petri dish: φ4.5 cm |
| Spores of *bacillus subtilis* | *Bacillus subtilis* NBRC3134<br>Vendor: National Institute of Technology and Evaluation |
| Spores of *bacillus subtilis* solution | Concentration: 10$^7$ CFU/ml, Quantity: 10 ml |
| Sterilizing lamp | HITACHI lighting Inc. GL15, Wavelength: 254 nm, Strength: 4.3 mW/cm$^2$ |
| UV light meter | TOPCON Inc. UD-25, UVR-25 |
| Reagent for measuring protein amount | Bio-rad Inc.-DC Protein Assay<br>(Protein standard: bovine gamma globulin) |

FIG. 5 illustrates *Bacillus subtilis* spores killing performance of the tested optimized filters.

Results: FIG. 5 confirms that the bare semi-HEPA filter does not show any inactivation in a dark condition, and requires UV light to achieve inactivation. A TiO$_2$ modified semi HEPA filter demonstrates the same behavior, but the inactivation effect of germicidal light is less than in the case of the bare semi-HEPA filter due to UV light absorption by the TiO$_2$ photocatalyst. A TiO$_2$/Ag modified semi HEPA photocatalyst has almost the same inactivation effect as the bare semi-HEPA filter under sterilizing light, but it also demonstrates spore inactivation in a dark condition. It has been demonstrated before that all filters have a trapping rate better than 99.98%. These data confirm that the elimination rate of trapped spores after 1 h is above 99.95 on an optimized TiO$_2$/Ag modified semi HEPA filter.

An example of a successful elimination of AMES strain *Bacillus anthracis* in liquid phase on the present invention catalyst is described.

Test Unit. The inventor in collaboration with Southwest Foundation for Biomedical Research (SFBR) challenged the present invention square column native photocatalyst with Anthrax Ames strain. The test setup consisted of two-6 W Hitachi FL6BL tubes mounted 1 cm above a flat stainless steel removable plate. The removable plate was used to hold the samples of the catalyst subjected to the test. The FL6BL tubes provided UV illumination (365 nm) of the catalyst samples. The whole setup was mounted inside a stainless steel box with a removable cover. Two internal fans were used for air recirculation.

Preparation of Test Unit. Twenty-four hours prior to the start of each trial, the test unit was sterilized. Following the sterilization, the test unit was placed in a biosafety cabinet in a BSL-3 facility for Anthrax challenge.

Experimental Design. *B. anthracis* (AMES) spores were applied to the TiO$_2$ catalyst test sheet in the liquid phase. Once dry, test strips were randomized into UV+ (365 nm) and Dark groups. Petri plates containing the catalyst test strips were then exposed to UV (or dark) within the test box. Test results are summarized in FIG. 6. The time points represent the duration of exposure to UV. Tests included (1) Anthrax test; (2) −bacteria, +UV control; (3)+bacteria, −UV control.

Figure 6:
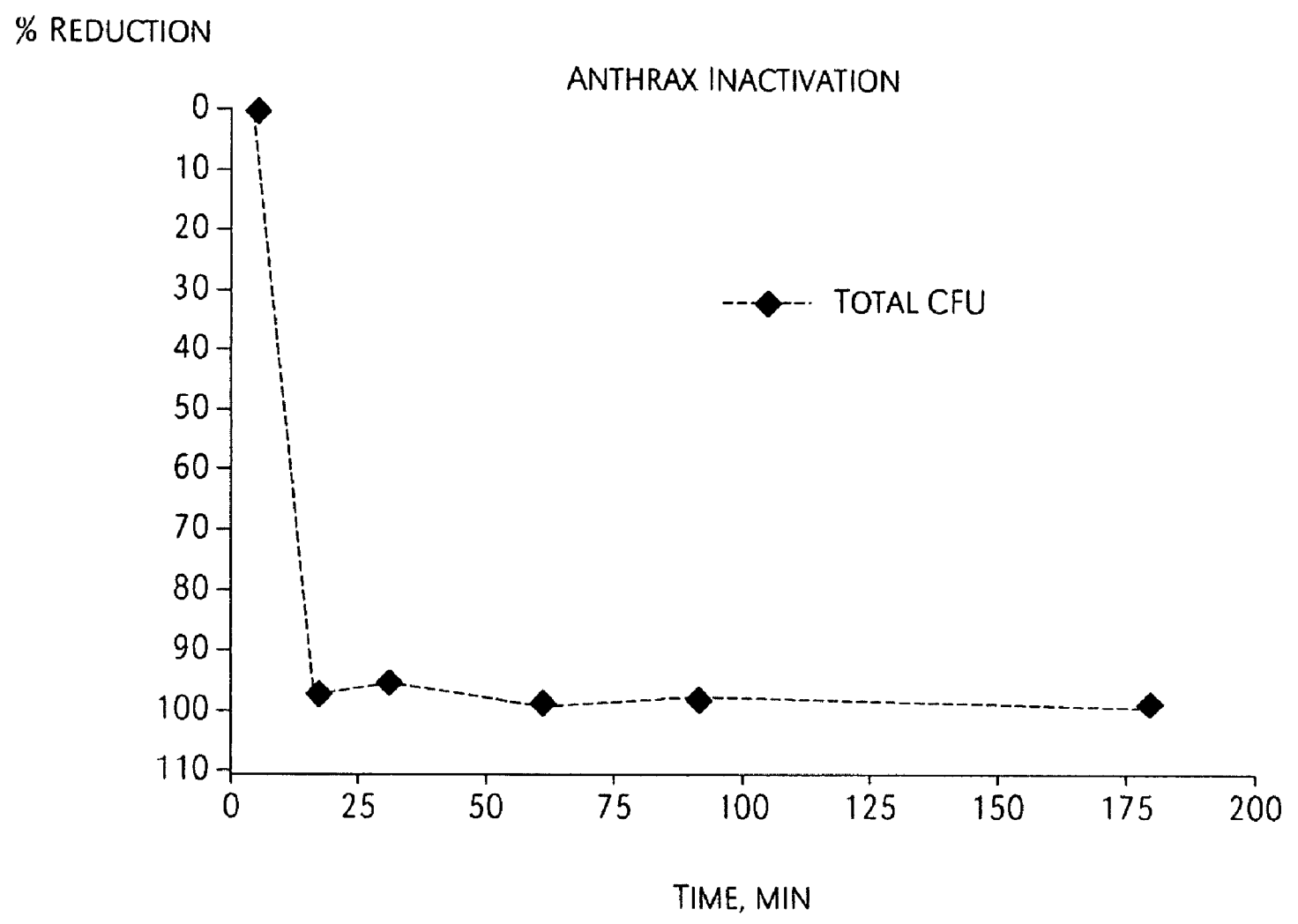

FIG. 6 illustrates a reduction of anthrax spores when immobilized on catalyst and exposed to UV light at 365 nm. % reduction shown.

Elution of test strip. At the completion of each time point, 3 ml of sterile PBS were added to the Petri dish containing the test strip. The strips were rocked for 15 minutes at 37 degrees Celsius. Serial dilutions of the eluted spores were then plated in duplicate onto tryptic soy agar plates containing 5% sheep's blood, then incubated at 37 degrees Celsius. At 16-18 hours after plating, eluted bacteria was enumerated and reported as total CFU.

Results and Discussion. At 15 minutes exposure to the UV source, a 99% inactivation efficiency was documented. Increased exposure of the catalyst to UV light for a 3 hour period resulted in a 99.5% inactivation rate.

Embodiment 3

Figure 4:
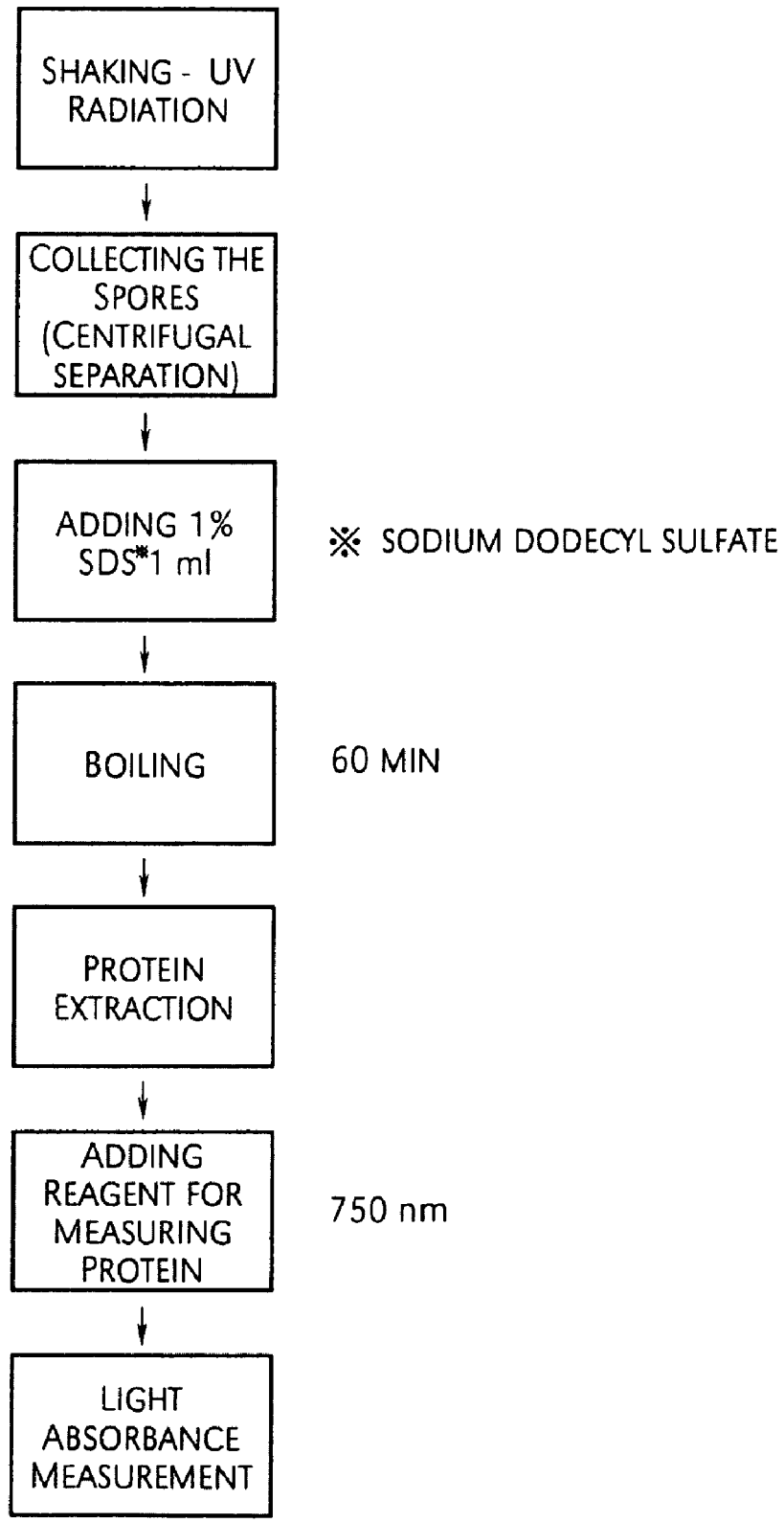
FIG. 4 illustrates a colorimetric procedure method flow chart.
Figure 7:
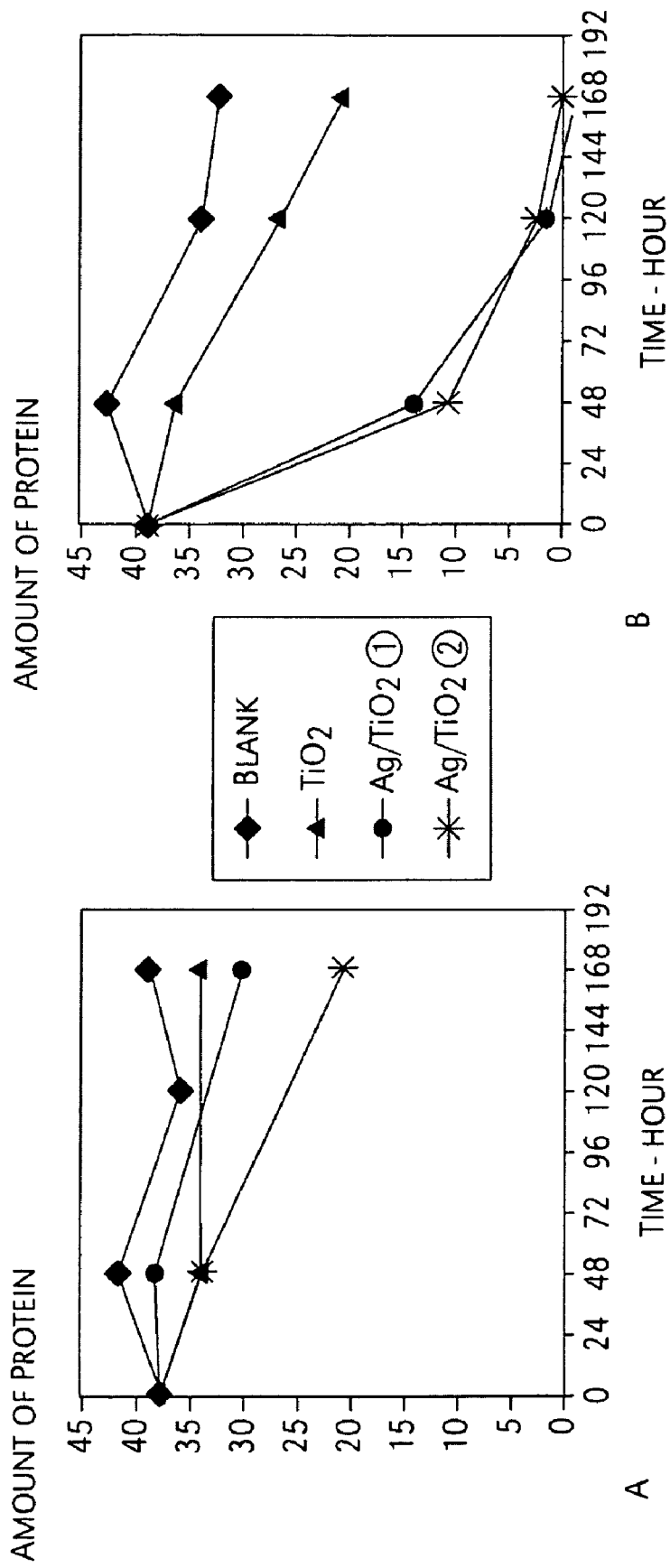
FIG. 7 shows results of a study of a colorimetric procedure used for the protein concentration determination is shown in FIG. 4 and Table 3.

Decomposition of the biological material into carbon dioxide and water:

Procedure: 10 ml Bacillus subtilis solution ($10^7$ pcs/ml) were transferred into four glass bottles. The semi-HEPA filter coated with $TiO_2$ was added to the second bottle. The semi-HEPA filter coated with Ag $TiO_2$ was added to the third and fourth bottles (Ag anchored volume in bottle 3:0.42 g/m²; in bottle 4:1.1 g/m²). All bottles were agitated under dark conditions. Another set of four bottles were charged in the same way and subjected to UV irradiation (254 nm) during the agitation. The samples of Bacillus subtilis solutions were collected at the time points of 48, 120, 168 hours for measuring the protein amount using DC Protein Assay (manufactured by Bio-rad Laboratories Inc.). The DC Protein Assay is a reagent used for measuring protein amounts based on the Lowry method. The colorimetric procedure used for the protein concentration determination is shown in FIG. 4 and Table 3. The results of the study are shown in FIG. 7.

Several conclusions can be drawn from the collected data:

1. The semi-HEPA filter coated with the $AgTiO_2$ photocatalyst—(silver loading 1.1 μm²) has a better protein decomposition effect than the $AgTiO_2$ filter with silver loading of 0.42 g/m² in a dark condition.

2. These semi-HEPA filters anchored with $AgTiO_2$ photocatalysts 1 and 2 increased further their protein decomposition performance under germicidal UV light illumination.

3. The semi-H EPA filter anchored with a $TiO_2$ photocatalyst without silver has a poorer protein decomposition performance than does the semi-HEPA filters anchored with silver.

As mentioned above, silver anchored to $TiO_2$ enhances not only inactivation performance, but also the decomposition performance of the collected spores of Bacillus subtilis. There are two theories explaining antibacterial properties of silver. The first theory, "Ion theory," describes silver ion (Ag+) as an antibacterial metal that reacts with the SH radical in the cell to inactivate the energy metabolism of the cell, resulting into cell death when Ag+ adheres to the protein such as at the cell membrane (enzyme). The other theory, "Active oxygen" theory, postulates that silver is working as a catalyst to decompose water molecules and create hydroxyl radicals that eliminate bacteria or virus.

Postulated the reason why the $AgTiO_2$ photocatalyst has good decomposition performance on the spores of Bacillus subtilis is based on the "Ion theory". At first, silver ion adheres to the spores of Bacillus subtilis, penetrates the shell and reacts with a protein enzyme to block the energy metabolism of the cell that inactivates the spores of Bacillus subtilis. The reaction of silver ion with various proteins contained within the spore provides disorders in the cell structure of the spore. From the second side, the hydroxyl radicals (.OH) created by the $TiO_2$ photocatalytic reaction will attack the outside of the spore to decompose it in stages. Furthermore, disorders in the cell structure of the spores allow the .OH radicals to easily penetrate the cell and to promote decomposition of the cell content.

Embodiment 4

Design of the photocatalyst capable of high efficiency collection of biological contaminants followed by inactivation of the collected biological material and decomposition to carbon dioxide, water, and, mineral acids/their salts:

The developed catalyst provides three stage mitigation of the biological threat. In the first stage the biological material (spores, bacteria, viruses) are collected on the surface of the filter (99.98% as demonstrated in Embodiment 1). After the biological material is collected, the catalyst, UV light and silver together provide efficient inactivation of the living organisms (99.95% in 1 hour as demonstrated in Embodiment 2). After that, the catalyst still acts on the collected and neutralized material and fully decomposes the material into carbon dioxide, water, and mineral acids/mineral salts (Embodiment 3). If any organic contaminants (cigarette smoke, sick-house syndrome, acetone, acetaldehyde, etc.) are present in the air stream, they will also be converted into carbon dioxide, water, mineral acids/mineral salts. Therefore, the catalyst provides three stage protection against biological contaminants and also improves the quality of the treated air.

Embodiments of the present invention will maintain good indoor air quality at homes, office buildings, airplane interior or automobile interior. In addition, the Embodiments of the present invention will mitigate attacks via HVAC systems on government buildings and high profile stationary targets.

In one example the invention demonstrated:
collection efficiency of 99.98% for Bacillus subtilis in a single pass.
99.95% inactivation rate of collected Bacillus subtilis spores after one hour under UV.
decomposition of the biological material by converting the material into water, carbon dioxide, and mineral acids and their salts.

In addition, in another example we achieved 99.5% inactivation of Bacillus anthracis (AMES strain) spores in 15 minutes.

What is claimed is:

1. A filter material for gas and liquid comprising:
a support layer;
a layer of binder on the support layer in which ionic silver and/or metallic silver particles are incorporated; and
a layer comprising particles of photocatalyst deposited on the layer of binder,
wherein loading of ionic silver varies from 0.1 to 10 grams per square meter of the filter material, and loading of photocatalyst particles varies from 1 to 100 grams per square meter of the filter material, and wherein the layer comprising particles of photocatalyst is a topmost layer adjacent to an ongoing flow of the gas or the liquid.

2. The filter material as in claim 1, wherein the support layer comprises glass fibers.

3. The filter material as in claim 1, wherein the support layer comprises semi-HEPA.

4. The filter material as in claim 1, wherein the support layer comprises HEPA.

5. The filter material as in claim 1, wherein the ionic silver is in a form of silver salts.

6. The filter material as in claim 1, wherein the binder comprises silica sol.

7. The filter material as in claim 1, wherein the photocatalyst comprises titanium dioxide.

8. The filter material as in claim 1, wherein the layer comprising particles of photocatalyst is the topmost layer relative to the layer of binder so that the layer of binder is not adjacent to the ongoing flow of the gas or the liquid.

9. The filter material as in claim 1, wherein the layer comprising particles of photocatalyst is in a position relative to the layer of binder so that the layer comprising particles of photocatalyst inhibits irradiation of the layer of binder by the UV radiation.

10. A filter material for gas and liquid comprising:
   a support layer;
   a layer of binder on the support layer in which ionic silver and/or metallic silver particles are incorporated; and
   a layer comprising particles of photocatalyst deposited on the layer of binder,
   wherein the layer comprising particles of photocatalyst is a topmost layer adjacent to an ongoing flow of the gas or the liquid so that the layer comprising particles of photocatalyst inhibits irradiation of the ionic silver and/or metallic silver particles by UV radiation.

11. The filter material as in claim 10, wherein the support layer comprises glass fibers.

12. The filter material as in claim 10, wherein the support layer comprises semi-HEPA.

13. The filter material as in claim 10, wherein the support layer comprises HEPA.

14. The filter material as in claim 10, wherein the ionic silver is in a form of silver salts.

15. The filter material as in claim 10, wherein the binder comprises silica sol.

16. The filter material as in claim 10, wherein the photocatalyst comprises titanium dioxide.

17. An apparatus of fluid treatment comprising:
   a chamber with an inlet and an outlet for flow of the fluid;
   a fluid filter positioned in the chamber so that the fluid is forced to flow through the fluid filter, wherein the fluid filter further comprises:
      a first layer incorporating silver particles therein positioned on a substrate; and
      a second photocatalyst layer positioned on the first layer incorporating the silver particles, wherein the second photocatalyst layer further comprises a material that is a strong absorber of UV radiation; and
   a source of UV radiation that irradiates the fluid filter, wherein the second photocatalyst layer is in a position between the first layer and the source of UV radiation so that the second photocatalyst layer inhibits passage of the UV radiation to the silver particles incorporated in the first layer.

* * * * *